(12) United States Patent
Monahan

(10) Patent No.: US 6,264,927 B1
(45) Date of Patent: Jul. 24, 2001

(54) TOPICAL SOLUTION AND METHOD FOR THE TREATMENT OF NAIL FUNGUS

(76) Inventor: Elmer P. Monahan, 397 Sandrock Dr., Craig, CO (US) 81625

( * ) Notice: Subject to any disclaimer, the term of this patent is extended or adjusted under 35 U.S.C. 154(b) by 0 days.

(21) Appl. No.: 09/384,721

(22) Filed: Aug. 27, 1999

Related U.S. Application Data

(60) Provisional application No. 60/098,126, filed on Aug. 27, 1998.

(51) Int. Cl.[7] .............................. A61K 7/04; A61K 33/18
(52) U.S. Cl. ................................ 424/61; 424/667
(58) Field of Search .............................. 424/61, 667, 642

(56) References Cited

U.S. PATENT DOCUMENTS

| | | | |
|---|---|---|---|
| 4,895,727 | * 1/1990 | Allen | 424/642 |
| 5,063,049 | 11/1991 | Billings | 424/61 |
| 5,346,692 | 9/1994 | Wohlrab et al. | 424/61 |
| 5,464,610 | 11/1995 | Hayes, Jr. et al. | 424/61 |
| 5,696,105 | 12/1997 | Hackler | 514/172 |

* cited by examiner

Primary Examiner—Thurman K. Page
Assistant Examiner—Blessing Fubara
(74) Attorney, Agent, or Firm—Sheridan Ross P.C.

(57) ABSTRACT

A composition and method for the treatment of nail fungus includes a first composition, including an ethyl ether component, and a second composition, including an iodine component, which when combined, form a highly penetrating anti-fungal solution. An infected nail is placed in the solution for from about 5 seconds to about 1 minute and then removed. Generally, one such treatment is sufficient to remove nail fungus from an infected nail, however, treatments may be repeated when necessary.

26 Claims, No Drawings

TOPICAL SOLUTION AND METHOD FOR THE TREATMENT OF NAIL FUNGUS

RELATED APPLICATIONS

This application claims priority from U.S. Provisional Pat. application No. 60/098,126 filed Aug. 27, 1998. The entire disclosure of the provisional application is considered to be part of the disclosure of the accompanying application and is hereby incorporated by reference.

FIELD OF THE INVENTION

The present invention is directed to a topical solution and a method for the treatment of nail fungus. In particular, the invention is directed to the treatment of onychomycosis.

BACKGROUND OF THE INVENTION

Onychomycosis is a fungal infection of the nail matrix, bed, or plate. Such fungal infections of the nail are difficult to treat, and recurrence is common. The reported incidence of the disease is from 2% to 14%, but the actual incidence is probably much higher. Dermatophytes, *candida* spp. and nondermatophytic molds (such as *Scytalidium dimidatum* and Scopulariopsis spp.) can infect nails and result in four major clinical presentations. The most common clinical presentation is distal and lateral subungual onychomycosis (DLSO), followed by total dystrophic onychomycosis (TDO), superficial white onychomycosis (SWO) and proximal subungual onychomycosis (PSO) which are often AIDS-associated.

Nails infected by onychomycosis become opaque, thickened, fragile and brittle. In addition, the growth of the fungus can actually lift the nail plate up and off the nail bed, causing pain for the patient. Eventually, loss of the entire nail may result from the disease.

Treatment methods for nail fungus have included surgical or chemical removal of the infected nail and treatment of the exposed nail bed with topical antifungals. Such treatments must be continued until the nail grows out, which can take six months or more. Although the cure rate for such surgical treatments is generally high, the procedure is painful and can result in permanent nail loss.

Other attempted treatment methods have included the use of disinfectant nail polish removers, such as is described in U.S. Pat. No. 5,063,049 to Billings. The composition disclosed in Billings combines a carrier or solvent made up of butyl acetate, ethyl acetate and isopropyl alcohol, combined with a fungicide of parachlormetaxylenol, and a bactericidal element consisting of thymol crystals.

Other inventors have utilized topical solutions. For example, U.S. Pat. No. 5,696,105 to Hackler discloses a topical creme containing mometasone furoate as a vasso constrictor.

Still other inventors have combined topical solutions with medicated devices. For instance, U.S. Pat. No. 5,464,610 to Hayes, Jr. et al., discloses the use of salicylic acid in a plaster preparation. This method allows for a continuous delivery of the active ingredient. U.S. Pat. No. 5,346,692 to Wohlrab et al. describes another method of continuously providing a topical agent to the infected nail. In Wohlrab, an antimycotically active substance and urea are combined with nail polish.

Despite prior attempts to treat onychomycosis, contentional topical treatments of nail infections has proven to be ineffective and oral antifungals suffer from various deficiencies, including safety and cost concerns. In addition, the topical application of known solutions generally must be continued for at least 10 weeks, and often must be regularly applied for an entire year. This is because the relative thickness of the nail plate inhibits penetration of topical applications. Additionally, compositions that are topically applied frequently are worn off of the infected area before they can penetrate the nail. Furthermore, recurrence of the infection is common once treatment ceases. Therefore, existing topical applications have proven less than satisfactory in treating nail infections.

Attempts at treating nail fungus have also been made using orally administered anti-fungal agents, but at significant economic and safety costs. The efficacy of such orally administered drugs, however, is limited due to the poor circulation of blood in the nail bed. As a result, treatment via oral methods requires high drug dosages over long periods of time. Such high dosages can have adverse side effects, and removal of the infection is often only temporary. As with known topical solutions, recurrence of the infection is common once the anti-fungal agents are no longer being administered. Because of hepatotoxicity and drug-drug interactions, these oral agents have played a limited role in the treatment of onychomycosis. Further, with the high drug costs, required laboratory testing and frequent office visits, many third party payers are limiting reimbursement for treatment to certain patients (diabetics, peripheral vascular diseases, history of lower extremity cellulitis, etc.).

In view of the above-described limitations of existing methods for the treatment of nail infections, a need exists for a new method for removing onychomycosis and other infections of the nail. The present invention addresses this need by providing a method and composition for reliably treating such infections from the nail without causing adverse side effects.

SUMMARY OF THE INVENTION

The present invention includes a method and composition for the treatment of nail fungus. In the method, an anti-fungal solution is typically applied to the infected nail. The topical solution is, in one embodiment, more specifically characterized as a first composition including an ethyl ether component, and a second composition including an iodine component. The ethyl ether component is used to penetrate the nail. The iodine component, carried in solution by the ethyl ether, then acts as a fungicide.

The method includes applying the above-described solution to the nail, or placing the infected nail in a reservoir of said solution, for a period of time. This single application of the described substance is typically successful in resolving the undesired nail fungus condition, however, the treatment may be repeated if necessary.

DETAILED DESCRIPTION OF THE PREFERRED EMBODIMENT

The present invention provides a solution and method for the treatment of particular infections of animals, such as nail fungus, by providing a first composition having an extremely low surface tension and a second composition having anti-bacterial, anti-viral and/or anti-fungal properties and having good solubility in the first composition. In so providing, the present invention overcomes the limitations of the previously known methods and compositions for the treatment of common infections and, in particular, nail fungus and other infections of the nail.

The present invention is generally comprised of a formulation that includes first and second compositions. The first composition includes an ethyl ether component, chosen due to its extremely low surface tension. The second composition is generally comprised of an iodine component because of its good solubility and because of its antiseptic properties. By providing a combination of these two components, a solution is created which allows anti-fungal agents to penetrate the nail bed and kill or otherwise incapacitate any existing fungus. In addition, this composition is benign from a toxicity standpoint, and does not produce adverse or lasting side effects in the patient.

In another embodiment of the present invention, the first composition my comprise ethyl ether. The second composition may comprise elemental iodine. A further embodiment may include a third composition comprising a pain reducing element, such as lidocaine or other similar pain relieving medications known in the art. Another embodiment includes a fragrance composition in the basic solution.

In a preferred embodiment of the present invention, the iodine and the ethyl ether are in a saturated solution. This result can be achieved simply by providing enough iodine that some remains as a solid when it is mixed with an amount of ethyl ether. In such a saturated solution the iodine will comprise between about 5% and about 30% of iodine by weight, and in a more preferred embodiment, includes iodine at approximately 21% of the solution by weight. Additional embodiments may include solutions having as little as about 5% of its weight as iodine. Preferred embodiments of a topical solution for the treatment of nail fungus include a first composition including an ethyl ether component and a second composition including an iodine component, wherein the first composition is present in at least about 3 times the quantity by weight of the second composition. Other embodiments include formulations where the first composition is present in about 8 times the quantity by weight of the second composition. Generally, the topical solution of the present invention may have the first composition consisting of 50% –95% ethyl ether and the second composition consisting, by weight, of from about 5% to about 30% iodine.

The method of the present invention consists of contacting the infected area (e.g., a person's nail) with the above-described solution. The affected nail, for example, can be contacted by soaking the nail for a period of at least about 10 seconds, and more preferably for at least about 1 minute. It has been found that one treatment is generally sufficient to remove and/or resolve the fungal infection from the nail. However, the treatment may be repeated as necessary.

Alternative embodiments of the present invention may include third compositions comprising gel forming agents or lotions. Such third compositions may serve to make the application of the first two compositions to the infected area (e.g., nail) more convenient. Additionally, embodiments of the invention include placing the described first and second compositions in a plaster solution. Such a plaster solution may then be applied directly to the nail or may be packaged on an adhesive strip. Once made part of an adhesive strip or bandage, the described solution may be applied to the nail by adhering the strip to the infected digit. Use of the present inventive composition in conjunction with bandages and/or structured supporting devices is believed advantageous in that a hard and/or resilient material can protect the nail while it is recovering from the fungal infection. It will occur to one skilled in the art that use of the present formulation in conjunction with absorbent material on which the formulation is impregnated may be useful in wrapping affected nails with suitable bandages, such as adhesive strips, self-adhering plaster preparations, etc. Indeed, one aspect of the present invention is directed to embodiments consisting essentially of such material treated with the above-described compounds and formulations, such material used by applying them directly to areas to be treated.

In yet further embodiments of the present invention, the formulation of the present invention can be impregnated and/or otherwise contacted with shoe soles in the toe region, medicated foot pads can be manufactured and even medicated socks can be produced wherein the present formulation is impregnated in such materials to treat as well as to act as a prophylactic to any nail fungus condition. Thus, such embodiments can be used not only to treat active fungal infections, but can also be used to avoid fungal infections from initiating and/or reoccurring.

Alternative embodiments of the present invention may include a first composition other than ethyl ether. For instance, any liquid having a low surface tension could be used in the first composition. Similarly, the second composition may consist of any fungicidal agent. All that is required is that the second composition, i.e. the fungicidal agent or antiseptic, be soluble in the first composition and that such agents do not alone or together cause pain or harm to the treated patient.

While the above particular embodiments find particular application in the treatment of fungal infections, the present invention is also useful in the treatment of infections in general, and particularly infections in humans and animals. Thus, the present invention should be understood as directed to formulations, specifications, application procedures, manufacturing procedures as described herein. The uses of such novel compositions include, but are not limited to, bacterial, viral and fungal infections, while being particularly useful for the treatment of onychomycosis. Moreover, it should be understood that the present invention finds veterinary applications as well as in the treatment of human beings. Various infections of companion animals, such as dogs and cats, are commonplace and can be treated with the present invention to remedy the effects of such infections, if not reduce the severity and/or reoccurrence of such infections. Other animals can also be treated with the present invention, including horses, sheep, cows and other commercially important animals.

The following experimental protocol is provided to illustrate how the present formulation works in practice. As a prophetic example, the protocol illustrates the use of the present invention to treat active nail fungal conditions.

EXAMPLE

There currently exists an unmet need for an effective, economical and safe topical product for the treatment of onychomycosis. This pilot study examines the efficacy of iodine/ether for the treatment of the most common clinical varieties of onychomycosis: DLSO and TDO.

Objectives

The objectives of this study are to evaluate the clinical and mycoloigcal cure rates in the treatment of distal/lateral subungual and total dystrophic toenail and fingernail onychomycosis.

Study Design

Single center, open trial of a saturated solution of crystalline iodine in ethyl ether (iodine/ether) topically applied (once or twice) to affected digit with contralateral untreated control digit.

Number of Patients/Study

Approximately 20 to 30 patients will be enrolled.

Study Drug Administration

Single concentration (saturated solution of crystalline iodine in ethyl ether) applied by digit immersion. Nail may be retreated at 30 days if no clinical changes are observed.

Efficacy Measures

The primary efficacy parameters will be:

percent of treated nails clinically clear at 6 months.

percent of mycologic cure (negative KOH and/or culture) at 6 months.

percent of nails exhibiting 50% in area of nail cleared at 6 months.

Safety Measures

The safety parameters will be derived from:

clinical examination (presence of periungual dermatitis, proximal nail dystrophy)

patient reports

Dose Selection and Method of Application

A saturated solution of crystalline iodine in ethyl ether will be applied to the affected nail by immersion of the distal phalanx for 60 seconds. A second immersion may be required if no clinical changes are observed at 30 days.

Patient Population

The study population will include ≧18 years old with bilateral DLSO or TDO and with +KOH and culture-proven dermatophytosis.

We will exclude:

pregnant or lactating women patients with known immune deficiencies (AIDS, chemotherapy, prednisone, organ transplant recipients)

patients with known iodine hypersensitivity patients with history of psoriasis, lichen planus, periungual eczemas which can result in onychodystrophy patients who have been treated with oral or topical antifungals within the past six months patients unwilling or unable to give consent for treatment, follow-up and photo documentation.

Concomitant Medications

Patients may not use topical antifungals or steroids during the 6 month evaluation period.

Clinical/Laboratory Evaluation

Clinical parameters to be collected will include: age, sex, weight, duration of onychomycosis, clinical presentation (DLSO or TDO or both). The affected contralateral nails will be noted with a triangular file at the proximal leading edge (DLSO) and the distance to the proximal nail fold noted. The nail will be assessed clinical, with standardized photography at 0, 30, 90 and 180 days.

Clinical parameters will include KOH and culture at 0 days and at 180 days. Speciation of the infectious pathogen may be performed by the laboratory.

Scheduling of Study Procedures

Screening visit will occur 1 month prior to enrollment and first treatment. Follow-up visits at 30, 90 or 180 days will be documented for each patient.

Preparation of final report will occur after the 180 day data collection.

| Procedure | Screening | Baseline | 30 d | 90 d | 180 d |
|---|---|---|---|---|---|
| Informed consent | X | | | | |
| Physical exam | X | X | X | X | X |
| Photo-documentation /nail measurements | | X | | X | X |
| KOH/fungal Cx | X | | | X | X |
| Adverse event monitoring | | X | X | X | X |

Wile various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. A topical solution for the treatment of nail fungus, comprising:
    a) a first composition consisting essentially of an ethyl ether component;
    b) a second composition consisting essentially of an iodine component;
    c) wherein said first component is present in at least about three times the quantity by weight of said second compositions.

2. The topical solution of claim 1, wherein said first composition substantially comprises ethyl ether.

3. The topical solution of claim 1, wherein said second composition substantially comprises elemental iodine.

4. The topical solution of claim 1, further comprising a third composition consisting essentially of a gel forming agent.

5. The topical solution of claim 1, wherein said first composition is present in about five times the quantity by weight of said second composition.

6. The topical solution of claim 1, wherein said first composition is present in about eight times the quantity by weight of said second composition.

7. The topical solution of claim 1, further comprising a pain-reducing composition.

8. The topical solution of claim 7, wherein said pain-reducing composition is lidocaine.

9. The topical solution of claim 1, further comprising a fragrance composition.

10. The topical solution of claim 1, wherein said first and second compositions are mixed with a plaster preparation, and wherein said plaster preparation is attached to a carrier.

11. The topical solution of claim 10, wherein said plaster preparation is self-adhering to a nail.

12. The topical solution of claim 1, wherein an absorbent material is impregnated with said solution.

13. The topical solution of claim 1, wherein an absorbent material is impregnated with said solution, and wherein said absorbent material is affixed to an adhesive strip.

14. The topical solution of claim 1, wherein said first composition consists of, by weight, from about 50% to about 95% ethyl ether, and said second composition consists, by weight, of from about 5% to about 30% iodine.

15. A topical solution for the treatment of nail fungus, consisting essentially of:
   a) a first composition consisting essentially of an ethyl ether component;
   b) a second composition consisting essentially of an iodine component;
   c) wherein said first component is present in at least about three times the quantity by weight of said second component.

16. The topical solution of claim 15, further consisting essentially of a third composition consisting essentially of a pain-reducing component.

17. The topical solution of claim 15, further consisting essentially of a third composition consisting essentially of a fragrance composition.

18. A topical solution for the treatment of main fungus, comprising:
   a) a first composition consisting essentially of an ethyl ether component;
   b) a second composition consisting essentially of an iodine component;
   c) wherein said second component is present in the first component as a saturated solution.

19. The topical solution of claim 18, wherein said second component is fully saturated in said first component.

20. A method for the treatment of nail fungus, comprising topically applying an effective amount of a composition as set forth in claim 1 to the nail fungus.

21. The method of claim 20, further comprising repeating said step of applying at least daily.

22. The method as set forth in claim 20, wherein said nail fungus is present on an affected nail and, wherein said affected nail is contacted by soaking the nail for a period of at least about 10 seconds.

23. The method as set forth in claim 20, wherein said composition consists essentially of from about 5% to about 30% iodine.

24. The method as set forth in claim 20, wherein said composition consists essentially of two components, ethyl ether and iodine, and wherein said iodine is present in an amount from about 5% to about 30% and said ethyl ether is present in an amount of from about 50% to about 95%.

25. The method as set forth in claim 20, wherein said composition is applied to the affected area in a plaster solution or on an adhesive strip/bandage.

26. The composition as set forth in claim 1, wherein said composition is used to treat non-human animals.

* * * * *